(12) United States Patent
Asbaghi et al.

(10) Patent No.: US 6,379,336 B1
(45) Date of Patent: Apr. 30, 2002

(54) PROTECTIVE DEVICE FOR INJECTION OR ASPIRATION NEEDLE

(76) Inventors: Hooman A. Asbaghi, 1114 Highland Dr., Del Mar, CA (US) 92014; Alidad Far Tash, 3900 E. Sunset Rd., #2085, Las Vegas, NV (US) 89120

( * ) Notice: Subject to any disclaimer, the term of this patent is extended or adjusted under 35 U.S.C. 154(b) by 0 days.

(21) Appl. No.: 09/336,405

(22) Filed: Jun. 18, 1999

(51) Int. Cl.[7] ................................................. A61M 5/32
(52) U.S. Cl. ...................................... 604/192; 604/198
(58) Field of Search ................................ 604/110, 192, 604/193, 194, 195, 196, 198, 260, 263, 506

(56) References Cited

U.S. PATENT DOCUMENTS

| | | | |
|---|---|---|---|
| 5,197,953 A | * 3/1993 | Colonna | 604/110 |
| 5,242,401 A | 9/1993 | Colsky | |
| 5,267,977 A | 12/1993 | Feeney, Jr. | |
| 5,295,975 A | * 3/1994 | Lockwood, Jr. | 604/198 |
| 5,364,362 A | * 11/1994 | Schulz | 604/115 |
| 5,376,080 A | * 12/1994 | Petrussa | 604/198 |
| 5,389,085 A | * 2/1995 | D'Alessio et al. | 604/110 |
| 5,403,286 A | 4/1995 | Lockwood, Jr. | |
| 5,478,316 A | * 12/1995 | Bitdinger et al. | 604/135 |
| 5,582,597 A | * 12/1996 | Brimhall et al. | 604/192 |

* cited by examiner

Primary Examiner—Richard K. Seidel
Assistant Examiner—Kevin C. Sirmons
(74) Attorney, Agent, or Firm—Nydegger & Associates

(57) ABSTRACT

A protective device for injection or aspiration needles has a barrel piece telescopically slidable over an adapter sleeve mounted at one end to the luer coupling of the syringe or to a multisample collector. An injection needle is mounted within the adapter sleeve, projecting out through an opening in the opposite nose end of the barrel piece. An interposed spring urges the adapter sleeve and barrel piece apart towards a fully extended position. The barrel piece and adapter sleeve are latched together in a ready to use position with the needle partially protruding out from the barrel piece. As the syringe or multisampling system is advanced, the needle is extended out through the barrel piece end to allow penetration into the patient's body, and automatic unlatching is induced as penetration begins. As the needle is withdrawn from the patient, the spring causes the needle to be fully withdrawn within the barrel, and locking features engage preventing any axial movement to insure permanent enclosing of the needle within the barrel piece and defeating any attempted reuse of the needle. A reference scale on the barrel piece aids in determining when the proper depth of penetration has been achieved.

12 Claims, 5 Drawing Sheets

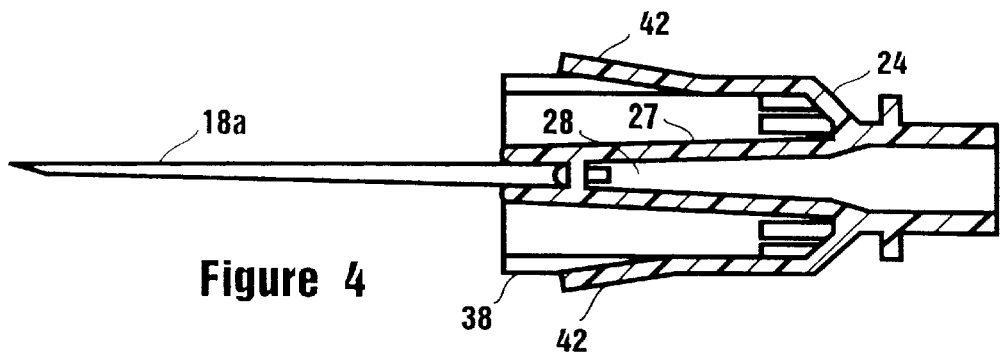
Figure 4
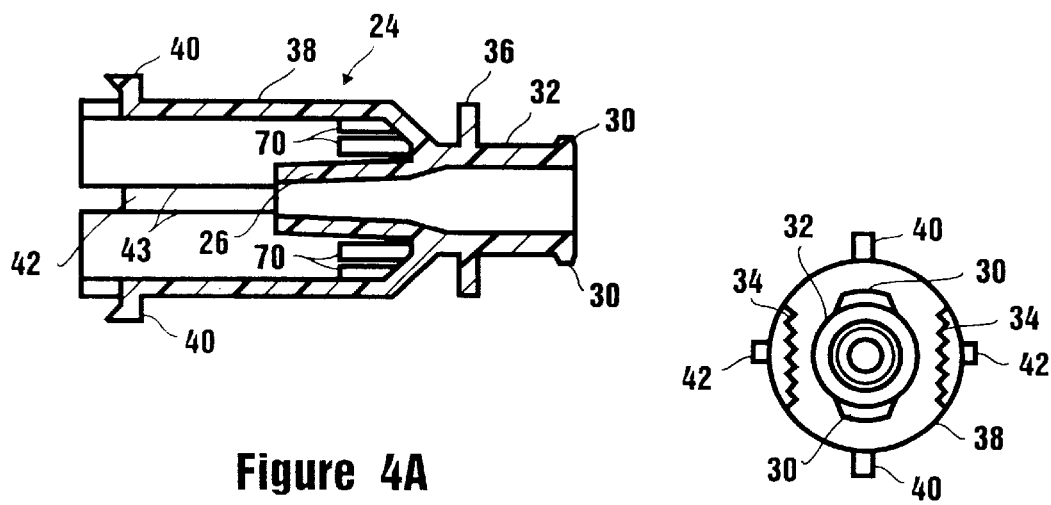
Figure 4A
Figure 5
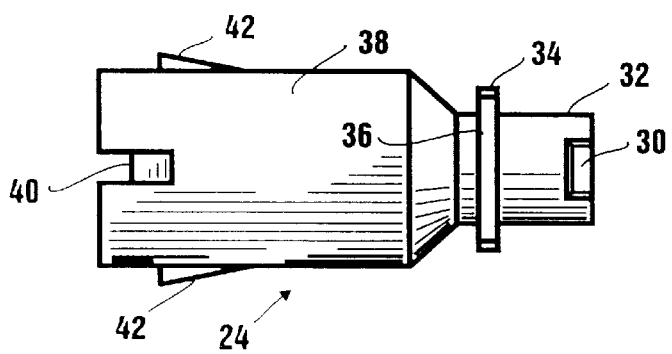
Figure 4B

PROTECTIVE DEVICE FOR INJECTION OR ASPIRATION NEEDLE

BACKGROUND OF THE INVENTION

This invention concerns protective devices for hollow injection or aspiration needles used in the practice of medicine to carry out injections of fluids into the body or to aspirate body fluids.

Such needles can become contaminated from contact with bodily fluids, and present a risk to medical personnel handling the used needles. It is also desirable to prevent reuse of a needle to prevent transmission of diseases to other patients.

These considerations have led to the development of various injection needle protective devices, as for example the guard shown in U.S. Pat. No. 5,688,241 issued to the present inventor on Nov. 18, 1997 for an Automatic Non-Reusable Needle Guard.

The device described in that patent required removal of the needle from the syringe or other holder for disposal.

U.S. Pat. No. 5,389,085 describes a protector which has the needle mounted to a protective cover so that the needle and cover can be removed together. However, that device does not provide a clear indication that the needle has been used nor positively prevent reuse.

It is the object of the present invention to provide an improved protective device of this type which clearly shows that a needle has been used and positively prevents reuse.

SUMMARY OF THE INVENTION

The above recited object and others which will become apparent upon a reading of the following specification and claims are achieved by a protective device for an injection or aspiration needle including an adapter sleeve, which has one end configured to be coupled to a syringe luer lock in place of the needle. The needle is mounted on a hub located within the adapter sleeve to project towards the opposite end of the sleeve. This protective device may be used in a similar manner with an aspiration needle of a multi-sampling system that uses evacuated blood collection vials or tubes.

A barrel piece also included in the device is slidable over the opposite end of the adapter sleeve with an interposed spring urging the barrel piece and adapter sleeve to move apart to a fully extended position and away from a fully nested, retracted position. In an intermediate latched condition, the barrel piece and adapter sleeve are held together resisting the force of the compressed spring by positioning a pair of radially projecting plugs on the adapter sleeve within latching cut outs in each of a pair of slots extending along the barrel piece length. The needle protrudes a short distance from a barrel nose portion with the device in the latched condition indicating an unused condition, and is covered with a cap preparatory to use. In use, as the needle penetrates into the patient's body, the adapter sleeve is advanced into the barrel piece which is restrained by contact with the patient's skin. The plugs are moved out of the latching cut outs and down the longitudinal slots until the full needle penetration desired is reached. A reference scale on the barrel piece aids the user in determining when the proper penetration depth has been reached. As the needle is withdrawn from the patients body, the spring causes the adapter sleeve to be withdrawn from the barrel piece, withdrawing the needle into the interior of the barrel piece. The plugs move along the slots until reaching a curved end surface, which cams each of the plugs into respective locking cut outs thereafter preventing axial movement of the adapter sleeve and needle. At this point, the needle tip is retracted completely into the barrel piece.

As the adapter sleeve is rotated to bring the plugs into the locking cut outs, a pair of deflectable strips protruding from the adapter sleeve are rotated into grooves in the barrel piece interior wall, permanently preventing rotation of the adapter sleeve to defeat any attempt to advance the plugs out of the locking cut outs.

The barrel piece has an opening through which the needle passes, and a sloping ridge surrounds the opening to tend to deflect the needle tip away from the opening to provide an additional measure preventing reuse of the needle.

The plugs both have a shape which overlies the edge of the slot through which the plugs slide when moving to the locked position to insure engagement with the slot edges is maintained.

DESCRIPTION OF THE DRAWING FIGURES

FIG. 4 is a longitudinal view of an adapter sleeve included in the protective device according to the invention, with an injection needle installed thereon.

FIG. 4A is a rotated sectional view of the adapter sleeve.

FIG. 4B is an external side view of the adapter sleeve.

FIG. 5 is an end view of the adapter sleeve.

DETAILED DESCRIPTION

In the following detailed description, certain specific terminology will be employed for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

Figure 1:
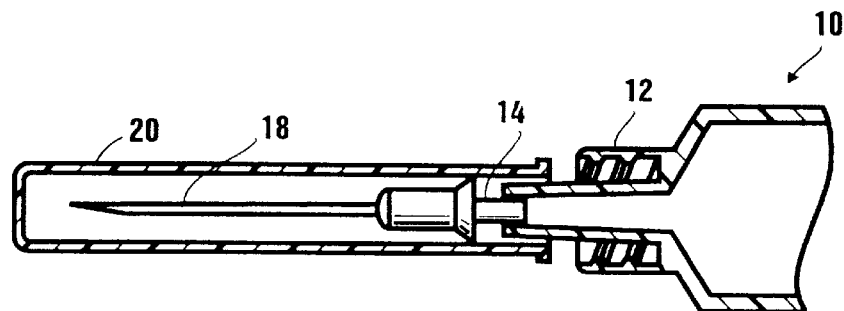
FIG. 1 is a fragmentary view in partial section of a front end of a conventional syringe with an injection needle and needle cover cap installed thereon.

Referring to FIG. 1, a front end portion of standard syringe 10 is shown, including a luer coupling end portion 12 adapted to connect an injection needle base 14 to the syringe 10 in the well known manner. The needle 18 is kept covered with a cap 20 until ready to be used.

Figure 2:
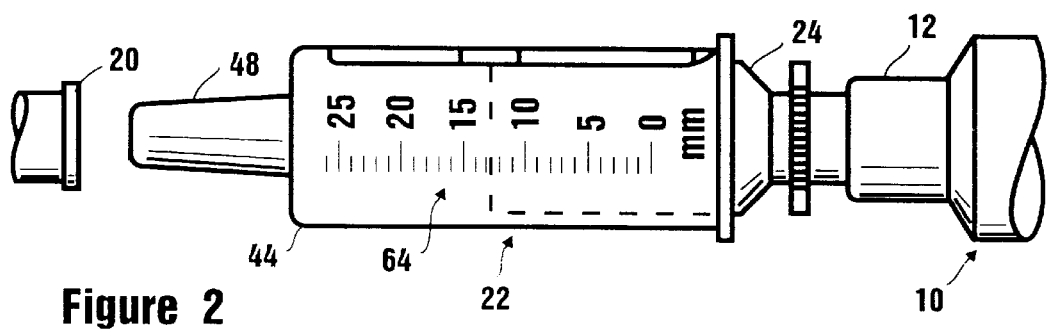
FIG. 2 is a fragmentary side view of a front end of a syringe having a protective device according to the invention installed thereon showing a penetration reference scale on the barrel piece included in the protective device.
Figure 3:
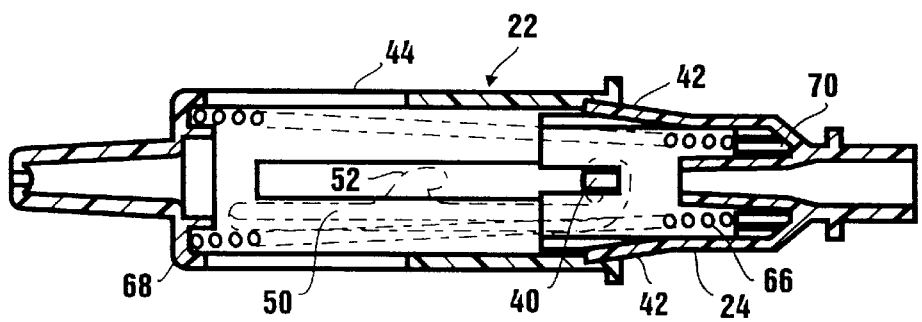
FIG. 3 is a sectional view of the protective device, depicting adapter sleeve and barrel piece components thereof nested together in a fully extended position, shown for clarity without the injection needle installed.
Figure 12:
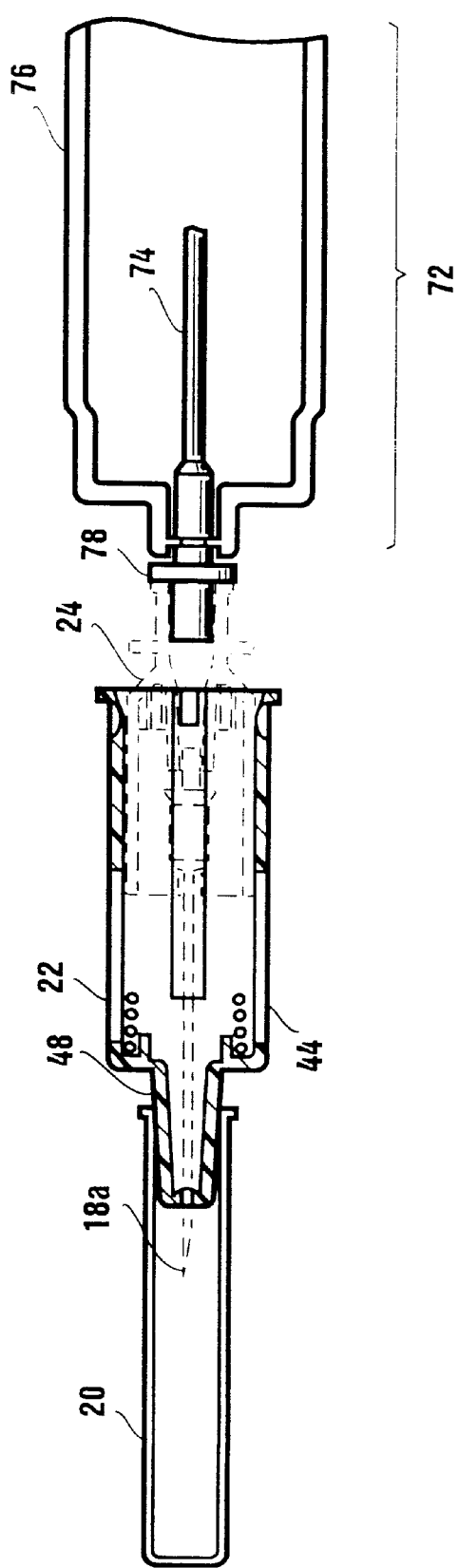
FIG. 12 is a side sectional view of the front end of an aspiration needle coupled to a multi-sampling system that would hold evacuated blood collection vials or tubes.

As shown in FIGS. 2 and 3, the protective device 22 according to the invention is installed on the luer coupling portion 12 in place of the needle 18. It should be understood that the invention is useable with an aspiration needle as well as an injection needle, where the aspiration needle may be coupled to a multisampling system (FIG. 12) that uses evacuated blood collection vials or tubes. This alternative embodiment illustrated in FIG. 12 shows the multisampling system 72 coupled to the protective device 22. More specifically, the adapter sleeve 24 is coupled to the multi-sampling adapter 78 by way of ultrasonic welding or by other means well known in the art. The adapter 78 is attachable to a holder 76 that would contain the evacuated blood collection tubes, as is well known. The multi-sampling adapter 78 has a needle 74 centrally located in the holder 76 that is used for puncturing the stopper of the evacuated collection tube during a fluid draw.

FIG. 4 shows needle 18A installed within a molded plastic adapter sleeve 24, using a taper mount 27 integrally formed within the adapter sleeve 24. The needle 18A may be mounted by ultrasonic welding of the taper mount 27, or by other manufacturing techniques. Alternatively, a standard male luer taper 26 may be integrally formed within adaptor sleeve 24, to which a standard needle and female luer (not shown) is attached (FIG. 4A). An inner passage 28 receives fluid being expelled from the syringe 10 and passes the same into the needle 18A.

FIGS. 4A, 4B and 5 illustrate a pair of lug projections 30 on the tubular end 32 which are designed to be threaded into the luer coupling 12 to create a fluid tight connection between the adapter sleeve 24 and the end of the syringe 10.

Grip features 34 on a flange 36 aid in installing the protective device 22 onto the luer coupling 12 of the syringe 10.

An outer tubular sleeve portion 38 has a pair of diametrically opposite radially projecting plugs 40, as well as a pair of outwardly biased resilient strips 42 formed by slits 43 located 90° from the plugs 40. The strips 42 are biased to tend to project radially out from the exterior of the sleeve portion 38 of the adapter sleeve 24, as shown in FIGS. 3, 4B and 5.

Figure 6:
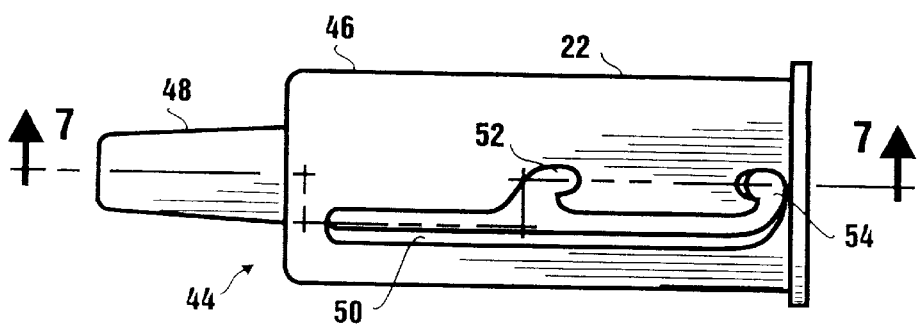
FIG. 6 is a side view of a barrel piece included in the device according to the present invention.
Figure 6A:
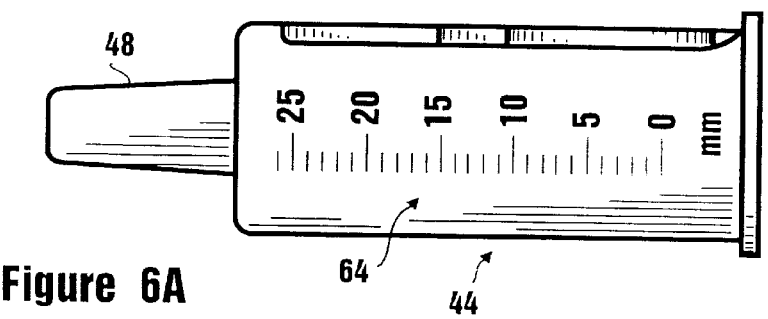
FIG. 6A is a rotated side view of the barrel piece.

FIGS. 6 and 6A illustrate a barrel piece 44 included in the protective device 22, telescopically received over the adapter sleeve 24. The barrel piece 44 has a main tubular portion 46 open at one end and a nose portion 48 formed on the other end.

A pair of lengthwise slots 50 are formed opposite each other on the main tubular portion 46.

A pair of latching cut outs 52, are formed extending out of each slot 50 at an intermediate axial location, and a pair of locking cut outs 54 are located at the end of each slot.

Figure 7:
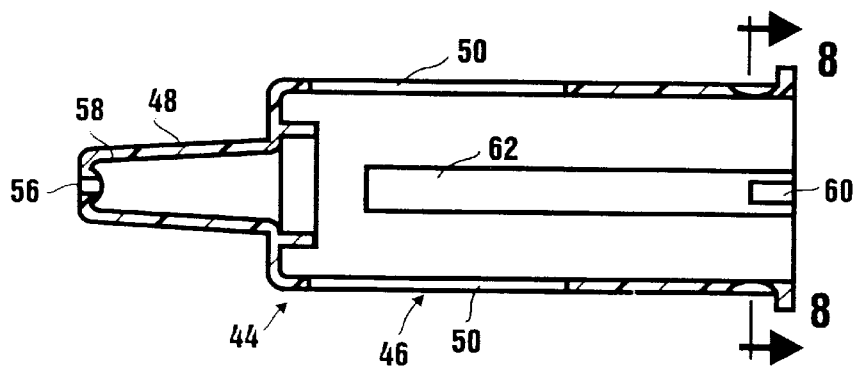
FIG. 7 is a longitudinal sectional view of the barrel piece.

As illustrated in FIG. 7, the nose portion 48 of the barrel piece 44 has an opening 56 which receives the needle 18A when it projects out of the barrel piece 44, with an outward sloping ridge 58 surrounding the opening 56 to tend to deflect the needle tip outwardly and thus defeat any attempted movement of the needle 18A out through the opening 56, as will be discussed further below.

Figure 8:
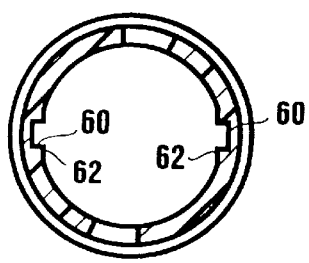
FIG. 8 is a view of the transverse section 8—8 taken in FIG. 7.

Continuing with an illustration in FIG. 8, a pair of diametrically opposed grooves 60 are each centered on a respective flat 62 formed within the interior of the barrel piece 44, the grooves 60 of a width sized to receive a respective one of the strips 42 as explained below. The flats 62 aid in molding the barrel piece and stiffen the barrel piece wall.

A penetration depth reference scale 64 (FIG. 2, 6A) may be provided along one side of the barrel piece 44. Since the barrel piece 44 is molded from transparent plastic, the position of the adapter sleeve 24 can be seen relative the scale 64 to aid in determining the depth of penetration of the needle 18A.

Figure 11:
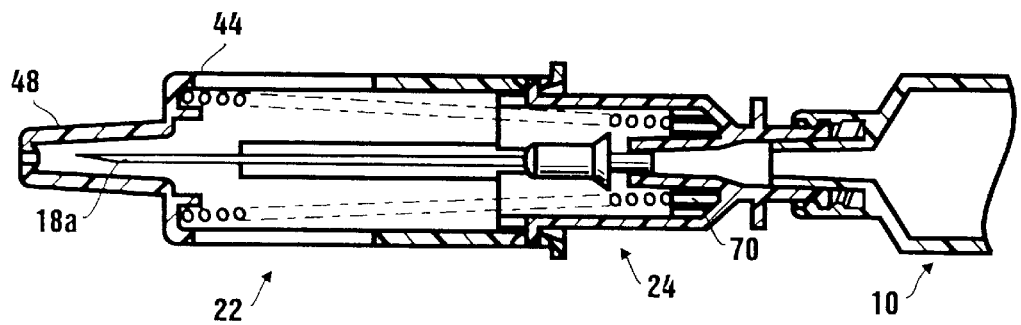
FIG. 11 is a sectional view of the front end of the syringe and the protective device after withdrawal of the needle and its complete retraction within the protective device.

The barrel piece 44 is telescoped over the adapter sleeve 24 so that the plugs 40 are received in the axial slots 50, with a helical compression spring 66 (shown only in FIG. 3) interposed between an end wall 68 of the barrel piece 44 and one end of a set of raised ridges 70 in the adapter sleeve 24 so as to urge the barrel piece 44 and adapter sleeve 24 to be moved to the fully extended position shown in FIGS. 3 and 11.

In the normal, ready to use position (FIG. 9), the barrel piece 44 and adapter sleeve 24 have been axially advanced to an intermediate position whereat the plugs 40 are rotated into latching cut outs 52 recessed from the slot 50 to hold the adapter sleeve and barrel piece components in that position, resisting the spreading force of the spring 66.

Figure 9:
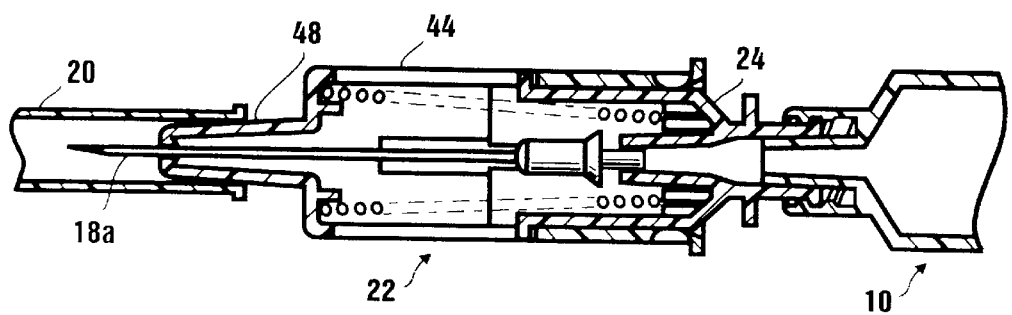
FIG. 9 is a side sectional view of a front end of a syringe having the protective device according to the present invention installed thereon, and in a position ready for use.

In this position, shown in FIG. 9, the needle 18A projects a short distance out of the nose portion 48 of the barrel piece 44, and a cap 20 is installed, pressed onto the nose portion 48. The protrusion of the needle 18A indicates that the needle 18A has not been used. Preferably, the distance of needle projection out of nose portion 48 is approximately 10 mm.

Figure 10:
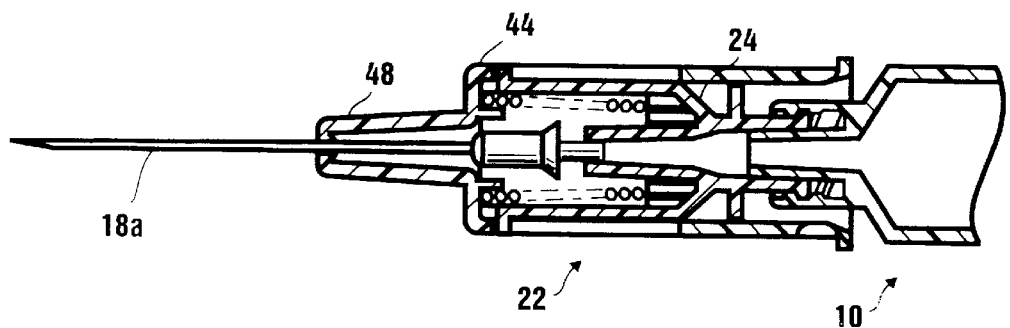
FIG. 10 is a side sectional view of the front end of a syringe and the protective device, shown with the needle fully advanced.

When readied for use, the cap 20 is removed as shown in FIG. 10. When the needle 18A is caused to penetrate into the patient's body, the nose portion 48 is pushed against the patient's skin, holding the barrel piece 44 stationary relative the adapter sleeve 24 as the needle 18A is advanced.

The forwardly sloping sides of each of the cut outs 52 allow the plugs 40 on the adapter sleeve 24 to automatically be moved out of the latching cut outs 52, the plugs 40 reentering the straight slot 50 and allowing the adapter sleeve 24 to move forward with the needle 18A as the syringe 10 is advanced to cause the needle 18A to penetrate into the patient's body.

Figure 3A:
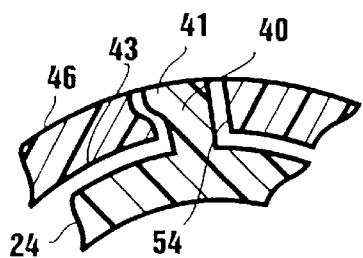
FIG. 3A is an enlarged fragmentary sectional view of a portion of the adapter sleeve and barrel piece showing an interlocking of one of the plugs and the edge of a slot cutout.

When the appropriate depth of penetration has been reached (aided by reference scale 64) the injection (or drawing of fluids) takes place, and thereafter the syringe 10 is withdrawn. As this occurs, the spring 66 continues to hold the barrel piece 44 against the patient's skin and the needle 18A is automatically retracted from the full extension position shown in FIG. 10 to a fully retracted position in which it is completely withdrawn into the interior of the barrel piece 44, as shown in FIG. 11. As this happens, the plugs 40 move down the slots 50 until reaching the curved end of the slot 50, contact therewith automatically camming the plugs 40 to rotate slightly to be caused to pass into locking cut out 54. As seen in FIG. 3A, the plugs 40 have a beveled overhang 41 which passes over a beveled edge 43 of the cut out 54 to insure that the plug 40 remains within the cut out 54 despite bulging of the wall of the barrel piece 44.

At this point, the strips 42, which have been confined within the main tubular portion 46 can expand out into grooves 60 as the barrel piece 44 rotates slightly to bring the grooves 60 and strips 42 into alignment. Thus, the barrel piece 44 and adapter sleeve 24 are locked together against any rotation in either direction preventing the plugs 40 from again becoming aligned with the slot 50. This keeps the plugs 40 captured in the locking cut outs 54 which are shaped to hook the plugs 40 and thereafter positively prevent any axial advance of the adapter sleeve 24 in the barrel piece 44.

Accordingly, the needle 18A is permanently kept completely confined within the barrel piece 44, precluding any accidental pricking of a person handling the used needle 18A and also preventing any attempt at reuse of the needle 18A. The covered position of the needle 18A also provides an indication that the needle 18 has been used.

The sloping side ridge 58 also will engage the tip of the needle 18A to deflect it outwardly if somehow the other locking features are overcome.

Thus, a simple, automatic, fail-safe protective device has been provided, which is simple but very reliable permanently preventing reuse of the needle as well as clearly indicating the unused or used condition of the needle.

What is claimed is:

1. A protective device for a hollow needle wherein the needle defines an axis and said device comprises:

an adapter formed with a luer fitting and at least one plug, said hollow needle being mounted on said adapter in fluid communication with said luer fitting with said plug extending from said adapter;

a barrel piece disposed on said adapter for reciprocal movement thereon, said barrel piece having a nose portion with an aperture for receiving said needle therethrough and said barrel piece being formed with a linear slot aligned substantially parallel to said axis with said plug inserted for movement within said slot, said slot having a first end and a second end with a latching cut out formed therebetween and a locking cut out formed at said second end; and a biasing means disposed between said adapter and said barrel piece to urge said adapter and said barrel piece in opposite axial directions and, in sequence, to initially hold said plug in said latching cut out to partially extend said needle from said barrel piece, to then allow said plug to move in said slot toward said first end to further extend said needle from said barrel piece, and to subsequently hold said plug in said locking cut out at said second end to cover and protect said needle with said barrel piece.

2. A device as recited in claim 1 further comprising a syringe engageable in fluid communication with said luer fitting.

3. A device as recited in claim 1 wherein said biasing means is a spring.

4. A device as recited in claim 1 wherein a first length of said needle extends through said aperture of said barrel piece when said plug is held in said latching cut out to partially extend said needle from said barrel piece, and a second length of said need extends through said aperture when said plug is moved into said slot and toward said first end to further extend said needle from said barrel piece, with said second length being greater than said first length.

5. A device as recited in claim 1 wherein said latching cut out is located approximately midway between said first end and said second end of said slot and wherein said plug extends outwardly from said adapter substantially perpendicular to said axis.

6. A device as recited in claim 1 further comprising a plurality of said slots and a plurality of said plugs with each said plug inserted into a respective said slot.

7. A device as recited in claim 1 further comprising a cap engageable with said barrel piece to cover said hollow needle while said plug is held in said latching cut out.

8. A method for protecting the tip of a hollow needle when used with a device to establish subcutaneous fluid communication between a patient and a syringe, wherein said device has said needle mounted on an adapter engageable in fluid communication with said syringe, a plug extends from said adapter, a barrel piece is disposed on said adapter for reciprocal movement thereon and said barrel piece has an aperture for receiving said needle therethrough and a linear slot aligned substantially parallel to said needle with said plug inserted into said slot, wherein said slot has a first end and a second end with a latching cut out formed therebetween and a locking cut out formed at said second end, and said device has a biasing means disposed between said adapter and said barrel piece to urge said adapter and said barrel piece in opposite axial directions, said method comprising the steps of:

piercing the skin of the patient with said hollow needle while said plug is held in said latching cut out by said biasing means to partially extend said needle from said barrel piece;

inserting said hollow needle into the patient to establish contact between said barrel piece and the patient;

continuing said inserting step to urge said barrel piece against the patient and move said plug into said slot and toward said first end to further extend said needle from said barrel piece; and withdrawing said needle from the patient to have said biasing means relocate said plug in said slot to said locking cut out to cover and protect said needle tip with said barrel piece.

9. A method as recited in claim 8 wherein said device further includes a cap engageable with said barrel piece to cover said hollow needle while said plug is held in said latching cut out, and said method further comprises the step of removing said cap prior to said piercing step.

10. A method as recited in claim 8 wherein said biasing means is a spring.

11. A method as recited in claim 8 wherein a first length of said needle extends through said aperture of said barrel piece when said plug is held in said latching cut out, and a second length of said need extends through said aperture when said plug is moved into said slot and toward said first end, with said second length being greater than said first length.

12. A method as recited in claim 8 wherein said latching cut out is located approximately midway between said first end and said second end of said slot and wherein said plug extends outwardly from said adapter substantially perpendicular to said axis, and wherein said device further includes a plurality of said slots and a plurality of said plugs with each said plug inserted into a respective slot.

* * * * *

UNITED STATES PATENT AND TRADEMARK OFFICE
CERTIFICATE OF CORRECTION

PATENT NO. : 6,379,336 B1
DATED : April 30, 2002
INVENTOR(S) : Hooman Asbaghi

It is certified that error appears in the above-identified patent and that said Letters Patent is hereby corrected as shown below:

<u>Column 5,</u>
Line 24-25, delete "1. A protective device for a hollow needle wherein the needle defines an axis and said device comprises:" insert
-- 1. A protective device which comprises: --
Line 26, insert -- a hollow needle wherein the needle defines an axis; --

<u>Column 6,</u>
Lines 10-13, delete "8. A method for protecting the tip of a hollow needle when used with a device to establish subcutaneous fluid communication between a patient and a syringe, wherein said device has said needle mounted ..." insert
-- 8. A method for protecting the user of a device when establishing subcutaneous fluid communication between a patient and a syringe, wherein said device has a hollow needle having a tip and mounted ... --

Signed and Sealed this

Twenty-ninth Day of October, 2002

Attest:

Attesting Officer

JAMES E. ROGAN
*Director of the United States Patent and Trademark Office*